United States Patent [19]

Thornton

[11] Patent Number: 4,993,421
[45] Date of Patent: Feb. 19, 1991

[54] CARDIAC MONITORING SYSTEM

[76] Inventor: William E. Thornton, 701 Coward's Creek Rd., Friendswood, Tex. 77546

[21] Appl. No.: 555,307

[22] Filed: Jul. 20, 1990

[51] Int. Cl.⁵ .............................................. A61B 5/02
[52] U.S. Cl. .................................. 128/670; 128/700; 128/696; 128/710
[58] Field of Search ............... 128/670, 700, 696, 736, 128/779, 710

[56] References Cited

U.S. PATENT DOCUMENTS

| | | | |
|---|---|---|---|
| 4,456,959 | 6/1984 | Hirano et al. | 128/700 |
| 4,803,996 | 2/1989 | Peel et al. | 128/696 |
| 4,830,021 | 5/1989 | Thornton | 128/779 |
| 4,860,759 | 8/1989 | Kahn et al. | 128/700 |
| 4,905,706 | 3/1990 | Duff et al. | 128/700 |

*Primary Examiner*—Francis Jaworski
*Assistant Examiner*—George Manuel

[57] ABSTRACT

A monitoring system for detecting and processing parameters affecting the cardiovascular system of a subject, and which includes a conventional Holter EKG recorder for long term electrocardiogram monitoring of the subject. In addition, the monitoring system includes sensors responding to certain physical activities and emotional states of the subject for generating electric signals representative of such activities and states. These electric signals are recorded in a separate recorder, or along with the EKG signals in the Holter recorder. The monitoring system includes a signal processor for correlating the signals from the sensors with predetermined coefficients so as to yield statistical data related to the physical activities and emotional states of the subject and to correlate signals representative of such activities and states with the EKG of the subject.

5 Claims, 8 Drawing Sheets

CARDIAC MONITORING SYSTEM

BACKGROUND OF THE INVENTION

Continuous, twenty-four hour or longer, electrocardiogram (EKG) monitoring (Holter) systems are widely used in the prior art for diagnosing heart disease. However, the long term prior art EKG monitoring systems are concerned only with EKG signals which is a major shortcoming.

There is another much simpler diagnostic means used in the prior art, namely the brief exercise "stress test" in which the EKG is recorded during a brief time interval while the patient is exercising strenuously on a treadmill. However this latter test is not comprehensive because exercise is only one of a number of stresses that can cause EKG abnormalities.

U.S. Pat. No. 4,830,021 which issued May 16, 1989 to the present inventor describes a locomotor activity monitoring system which includes EKG and which involves long term monitoring of the patient. The system described in that patent, unlike other prior art cardiac monitoring systems, uses EKG only incidentally and primarily to monitor heart rate.

There are shortcomings in each of the prior art systems referred to above. For example, the Holter system has no detection/recording capability other than time, EKG readings and a patient marker. The patient maintains a time related diary of such events. At best the approach is qualitative. It is also incomplete, since no data is entered, for example, when the patient is asleep. In essence, there is no objective or recorded evidence of any patient activity.

The cardiac abnormalities which are revealed by the prior art cardiac monitoring systems are equated only to physical activities. However, such cardiac abnormalities may also be revealed by a number of other conditions in the body. Knowledge of these conditions, other than physical activity, which provide detectable cardiac abnormalities is frequently important for determining the proper treatment. As noted above, such knowledge can not be acquired from current cardiac monitoring systems and techniques. Copending application Ser. No. discloses a cardiac monitoring system which in addition to physical activities also monitors such other conditions.

It is well known, for example, that inadequate blood supply to the heart may alter a portion of the EKG known as the S.T. segment. The best known cause of inadequate blood supply to the heart is partial closure of one or more arteries by fatty formations. Limited blood flow through a narrowed artery which is inadequate to meet the needs demanded by exercise is a common cause of such EKG changes. However, normal or slightly affected arteries may produce the same effect due to spasms from emotional upsets which are transmitted to the heart by the nervous system. The prior art cardiac monitoring systems offer no aid in differential diagnosis of this problem. The treatment in the case of clogged arteries is normally surgery, but a vastly different treatment is required in the case of arterial spasm caused, for example, by emotional upsets in relatively normal arteries, or even arteries which are partially occluded.

One objective of the present invention is to provide a relatively simple and practical system which detects and records parameters affecting the cardiovascular system of a subject simultaneously with the recording of the EKG data. Should EKG abnormalities be detected, the system of the invention analyzes and correlates physical and emotional activities of the subject and environmental parameters which could cause such abnormalities.

As pointed out in the Copending Application, external events known to cause cardiovascular problems include: physical stress; work; exercise; temperature extremes and changes; and fatigue. In addition, there are emotional stresses which also can cause cardiovascular problems, and these include, for example, such emotional stresses as real or perceived danger, anger, conflict, and the like.

Since it is impractical for a monitoring system to record indications of all of the parameters set forth in the preceding paragraph, some means for detecting, recording and correlating the parameters with respect to EKG abnormalities is required, and an objective of the present invention is to provide a practical system which uses correlation techniques for furnishing data concerning all of the circumstances set forth above as related to EKG changes. This latter objective may be achieved in conjunction with existing Holter EKG monitoring systems.

In the system of the invention, raw data relating to the parameters discussed above may be detected and recorded together with EKG data in a Holter magnetic tape recorder. Alternately, the raw data may be recorded in a separate magnetic tape recorder. In either event, in the system of the invention, the data is reduced, analyzed and correlated on replay. As a second and preferred option, the raw data may be detected and reduced at the monitoring site, and only pertinent specially encoded parameters recorded in the Holter or separate recorder, with the encoded parameters being detected and cross-correlated on replay. As a third option, raw data may be detected and analyzed at the patient's recording level, encoded in existing EKG format, recorded on an existing EKG channel in a Holter recorder, and detected by existing replay means and translated and correlated with the EKG data. In addition, analyzing and correlating data may be reduced with analyzed EKG data at the recorder level, with only the results being stored in the recorder.

For example, and as described in Copending application Ser. No. (K 3423) a prior art four-channel Holter magnetic tape recorder may be provided, three channels of which may be used to record EKG signals, and the fourth channel used to record time signals and additional patient data in multiplexed digital and other encoded form. This additional patient data may then be stored/analyzed in a digital computer which correlates the data and produces a report which contains, for example, a summary of the EKG data such as heart rate, S.T. level, plots of the data, examples of abnormal EKG activity, and potential diagnosis based on the data. By adding data related to physical and emotional stresses in accordance with the present invention, the specificity and the reliability of the diagnosis and treatment can be increased.

The system disclosed in the Copending application Ser. No. (K 3394), in addition to collecting ambulatory data such as described in U.S. Pat. No. 4,830,021 also collects additional data relating to activities which also affect or define cardiac responses of the subject. As described in Copending application Ser. No. (K 3394), these additional activities may include, for example, verbal exchanges, evidence of emotional stress arising from verbal exchanges between the subject and others, emotional stress arising from dreams, and other physical conditions such as the posture of the subject, air temperature, ambient light level, elapsed time, and so on. The resulting data is analyzed and correlated in the system of the present invention preferable as the actual report is generated by the system.

SUMMARY OF THE INVENTION

A monitoring system for detecting and processing parameters affecting the cardiovascular system of a subject. The monitoring system includes a conventional Holter EKG recorder for long term electrocardiogram monitoring of a subject. In addition, the monitoring system includes sensors responding to physical and emotional activities of the subject for generating electric signals representative of such activities. These electrical signals are recorded along with the EKG signals either in the Holter recorder or in a separate recorder. Finally, the monitoring system includes a signal processor for correlating the signals from the sensors with redetermined coefficients to yield statistical data related to the activities of the subject and to correlate such data with the EKG of the subject.

DETAILED DESCRIPTION OF THE ILLUSTRATED EMBODIMENT

Figure 1:
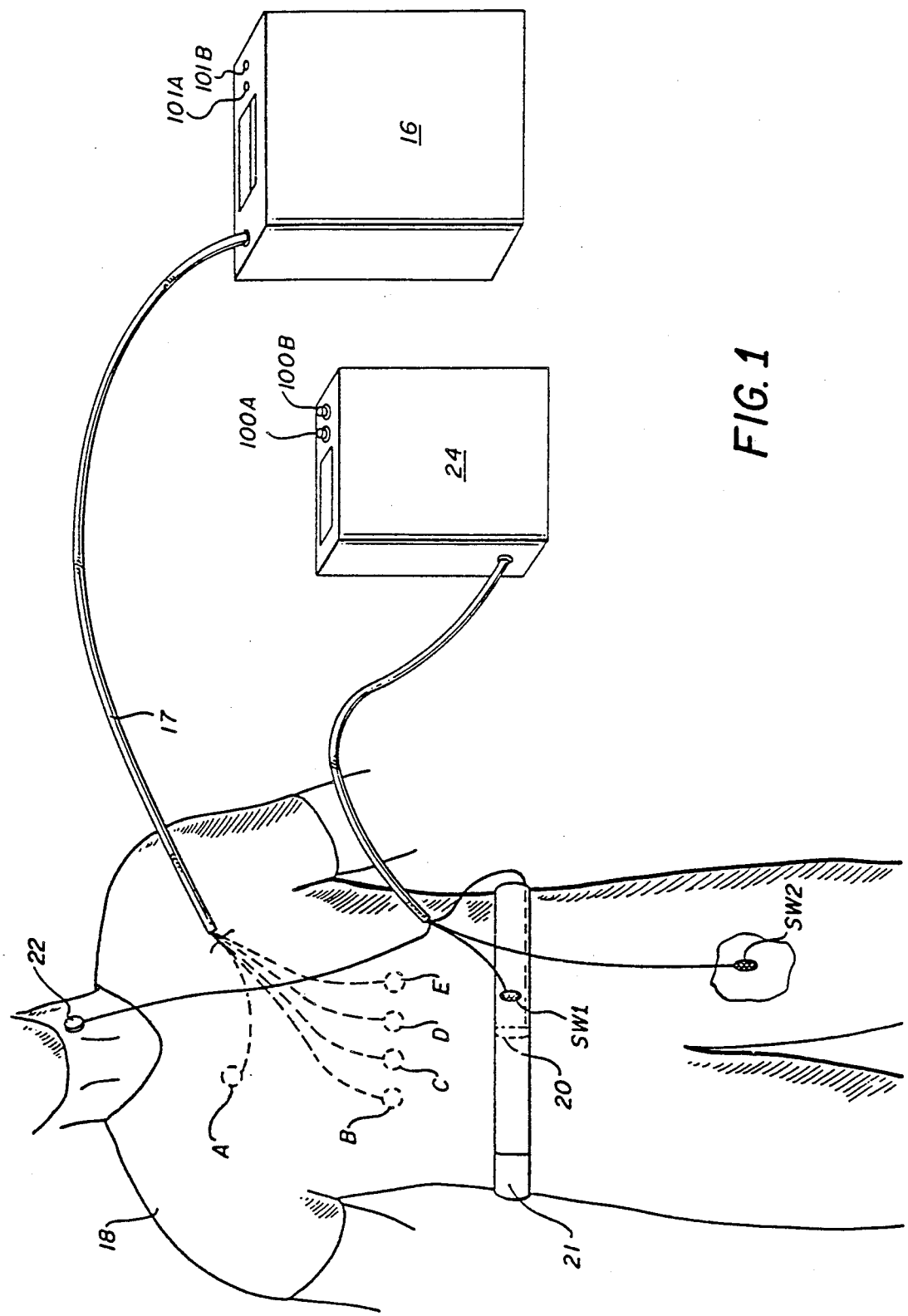
FIG. 1 is a representation of a subject on which various sensors and other instruments are mounted for carrying out desired cardiac monitoring functions.

In order for the Augmented Holter Monitoring (AHM) system of the invention to perform its desired monitoring functions, it is necessary for the subject 18 of FIG. 1 to carry certain sensors, transducers and other equipment, as described in Copending application Ser. No. (K3394). For example, the subject 18 may carry an existing miniature EKG Holter recorder 16 in one of his shirt pockets. Usual EKG electrodes A–E are mounted on the subject and connected to the Holter recorder 16 over leads 17. The subject 18 also carries a miniature accelerometer 20 on a belt 21, the accelerometer measuring vertical accelerations (Gz) of the subject at his center of gravity. The accelerations (Gz) are converted to vertical forces (Fz) by the system in a manner fully described in U.S. Pat. No. 4,830,021.

Two position sensor switches SW1 and SW2 are also attached to subject 18, one at his waist and the other on his thigh. Switches SW1 and SW2 may be commercially available mercury gravity switches, or other appropriate gravity switches may be used. These switches serve to provide indications of the posture of the subject, specifically whether the subject is standing, sitting or lying down. The operation of such switches is described in some detail in U.S. Pat. No. 4,830,021.

As also described in Copending application Ser. No. (K3423), a multiple sensor 22 is mounted on the neck of subject 18. This multiple sensor may include two microphones, as will be described, as well as light and temperature sensors. The light sensor may be a simple photodiode circuit which generates electrical signals indicative of ambient light levels. The temperature sensor may be a thermistor circuit which generates electrical signals indicative of ambient temperature. The sensors 20, SW1, SW2 and 22 are all connected to a second recorder 27 which may fit into a second shirt pocket of subject 18, or which may be clipped to the Holter recorder 16. Alternately, recorder 24 may be combined in Holter recorder 16.

Figure 2B:
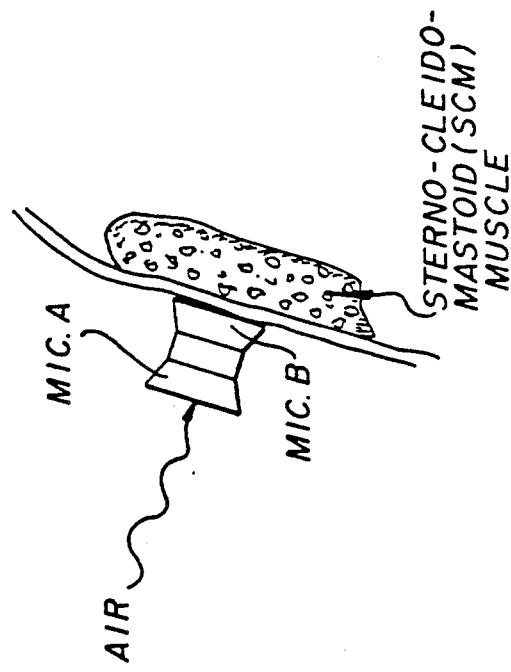
FIGS. 2A and 2B constitute a further representation of the subject shown in FIG. 1, and show the manner in which first and second microphones are mounted on the subject for purposes to be explained, FIG. 2B being a section taken along the line 2B—2B of FIG. 2A.
Figure 2A:
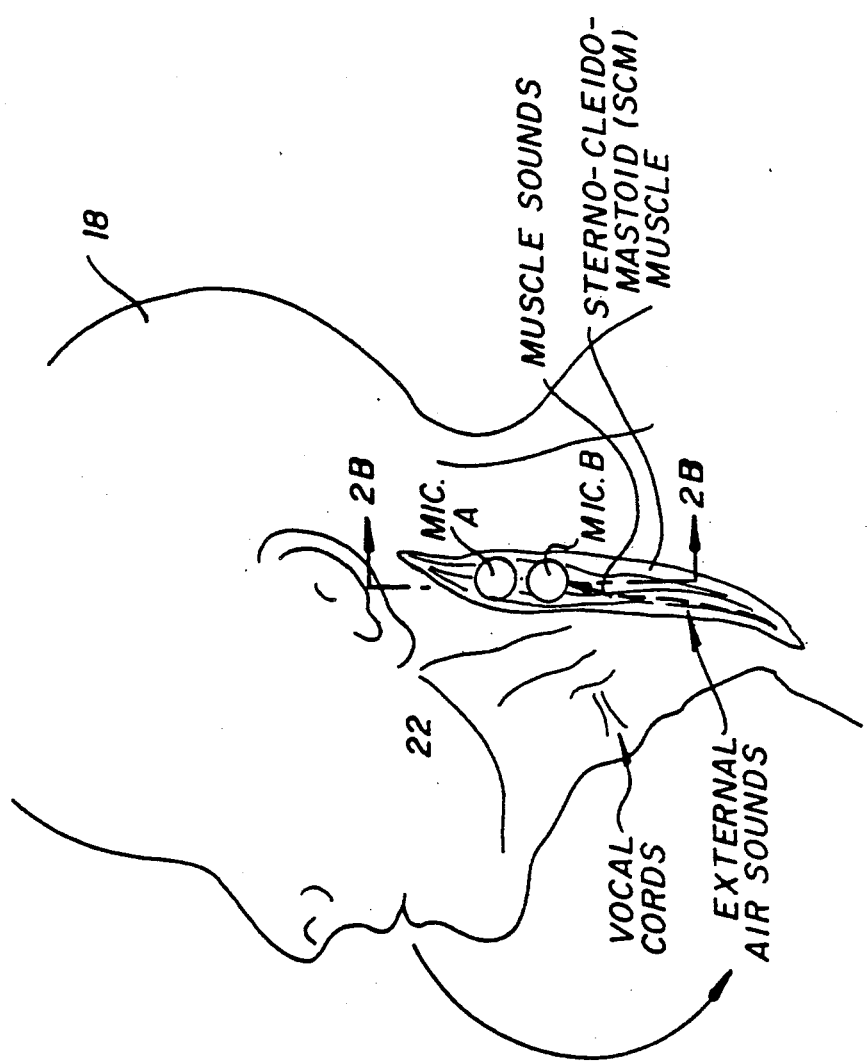

As shown in FIGS. 2A and 2B, and as described in Copending application Ser. No. (K3423), composite sensor 22 includes two microphones designated Mic "A" and Mic "B". Microphones Mic "A" and Mic "B" may be sub-miniature microphones of the dynamic, electret or semiconductor type, and preferably have frequency responses in the range of 20–3000 Hz. Microphone Mic "B" is attached to the neck of subject 18 adjacent to the sterno-cleido-mastoid (SCM) muscle above the collar. Microphone Mic "B" registers strong vibrations from the voice of subject 18 (0.3–3 KHz); weaker vibrations from external sources including voices (0.3–3 KHz); and lower frequency vibrations due to muscle contractions of the subject occurring, for example, when the subject is asleep and dreaming. Microphone Mic "B" should have a high low frequency response at approximately 10 Hz to respond to the low frequency (16 Hz) muscle activity.

Although the microphones Mic "A" and Mic "B" are shown displaced from one another in FIG. 2A, microphone Mic "A", is preferably mounted on microphone Mic "B" as shown in FIG. 2B, and the microphones are acoustically isolated from one another. Microphone Mic "A" serves to register the speech of the subject as transmitted through air, and it also registers other sounds transmitted to it by air.

Figure 3:
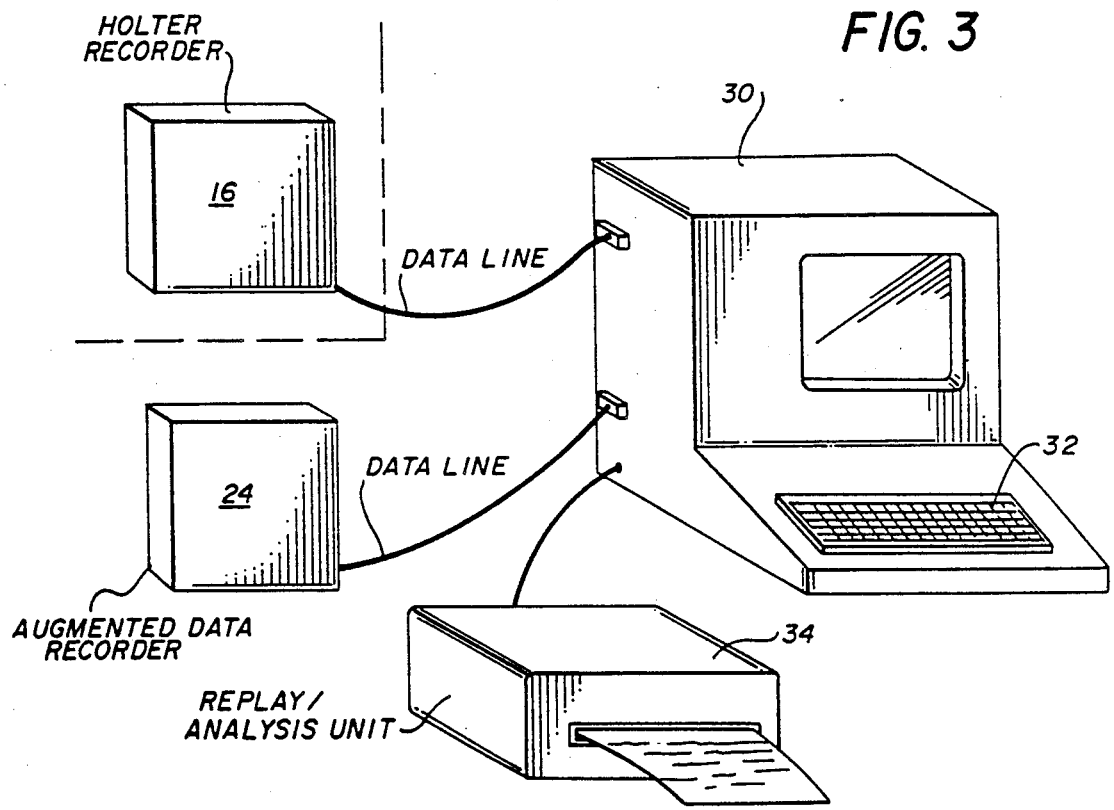
FIG. 3 is a block diagram of a Holter replay/analysis unit which is used to receive data from recorders carried by the subject of FIG. 1.

A processing and correlating unit 30 is shown in FIG. 3. The recorders 16 and 24 of FIG. 1 are connected to unit 30 during replay, as shown, and data recorded on recorders 16 and 24 is fed into the unit. Unit 30 includes all usual components, including a computer, controls, displays, a keyboard 32 and a printer 34, all of which are needed for processing, correlating and displaying the augmented Holter data from recorders 16 and 24. The augmented Holter data from the recorders (which must be time tagged) is digitized and stored in unit 30.

Correlation and analysis of the data from recorder 24 by unit 30 serves to yield substantial amounts of information on the activity of subject 18 of FIG. 1, and of the environment surrounding the subject. An important feature of the analysis and in accordance with the teaching of the present invention, is that no attempt is made for an absolute analysis, but rather to provide a statistical statement using estimated or known correlation coefficients with respect to the various parameters. In this manner, the probability of the occurrence of any particular event is provided to the physician without the need for excessively large and/or complicated equipment.

The vertical acceleration (Gz) outputs of accelerometer 20 of FIG. 1, which represents the locomotor activity of the subject, has a characteristic waveform which varies synchronously both in frequency and amplitude with the step frequency of the subject. Accordingly, it is important that the values of these two characteristics of the waveform be recorded in recorder 24. The system response of the body is such that a sample rate of one per minute, that is, the number of steps and mean force is adequate. A circuit for achieving the foregoing may be incorporated into recorder 24. Such a circuit is shown in the block diagram of FIG. 4.

Figure 4:
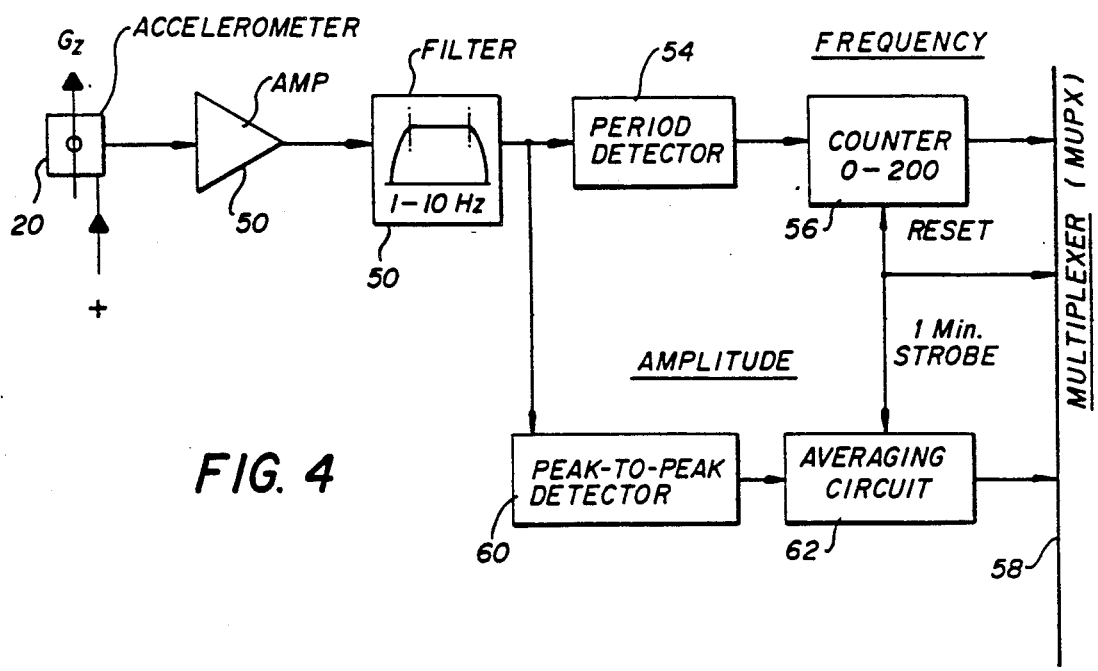
FIG. 4 is a block diagram of the manner in which vertical acceleration signals of the subject are processed.

In FIG. 4, and as described in Copending Application Ser. No. (K 3423) filed in the name of the present inventor, accelerometer 20 is connected to an amplifier 50 which, in turn, is connected through a bandpass filter 52 to a period detector 54. The period detector 54 is connected to a counter 56 for detecting the frequency of the waveform. The output of counter 56 is connected to a bus 58 which carries the signals from the counter to an appropriate multiplexer (MUPX). Filter 52 is also connected to a peak-to-peak detector 60 for detecting the amplitude of the waveform. The output of peak-to-peak detector 60 is connected to an averaging circuit 62 whose output is also connected to bus 58. Counter 6 and integrator circuit 62 are each reset by an appropriate one minute strobe, as shown. The multiplexer MUPX causes the data from the circuit of FIG. 4 to be recorded in recorder 24, multiplexed with other data from the sensors of FIG. 1. All of the data is preferably recorded in digital form.

Figure 5:
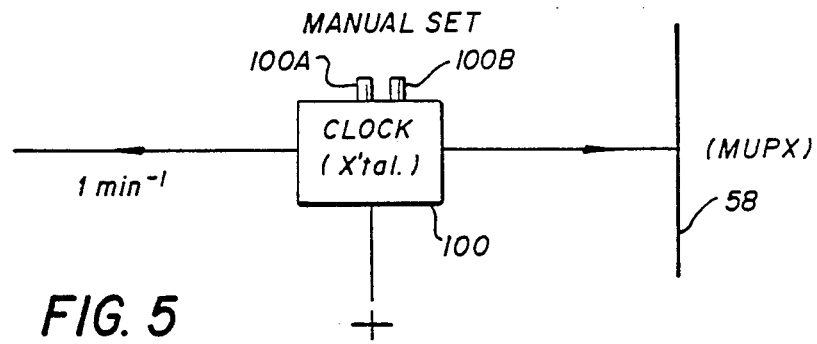
FIG. 5 is a block diagram of a master digital clock which is included in the recorders forming a part of the system.

A crystal time clock 100, as shown in FIG. 5, is included in recorder 24. The time clock may include the usual manual set controls 100A, 100B which are also shown in FIG. 1. Discrete twenty-four hour time signals and a 1 min-1 code is generated by the clock 100. The discrete time signals are introduced to bus 58 which carries the signals to the multiplexer MUPX to be recorded in digital form in recorder 24 multiplexed with the other digital data. A similar time clock may be included in recorder 16 (FIG. 1) with manual time set controls 101A and 101B. Such a clock would produce only time signals in a single unit recorder.

Figure 6:
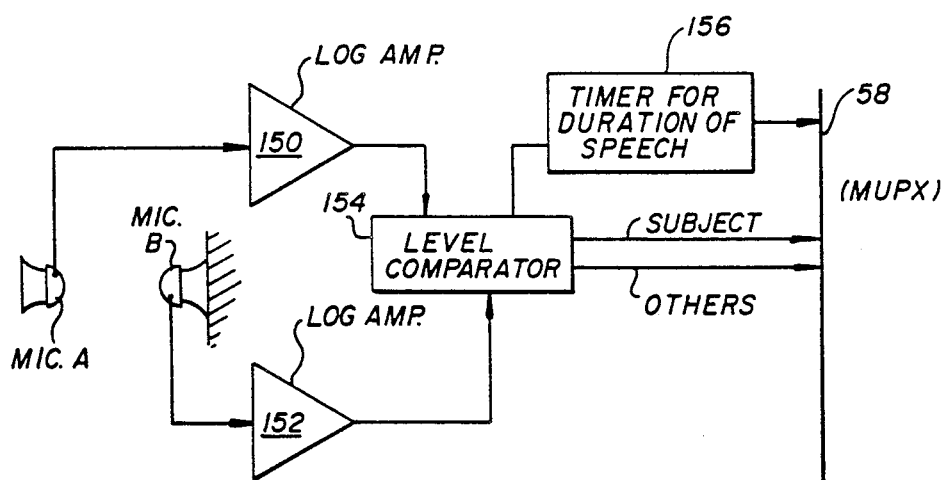
FIG. 6 is a block diagram showing the manner in which signals representing the speech of the subject and others are processed in the system.
Figure 7:
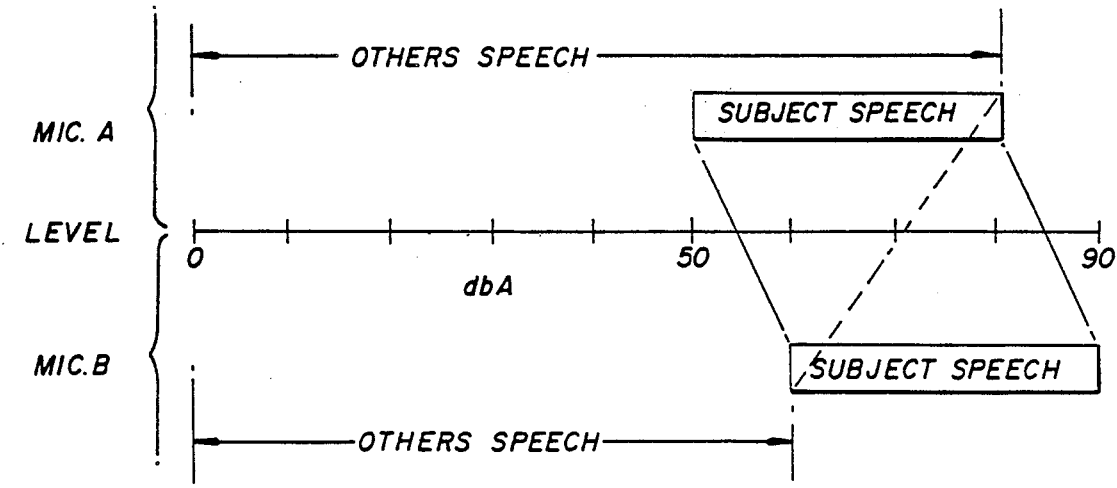
FIG. 7 is a schematic representation of the incidence of speech by the subject and by others monitored by the system.

As also described in Copending Application Ser. No. (K 2423), outputs from microphones Mic "A" and Mic "B" of FIGS. 2A and 2B are amplified by respective log amplifiers 150 and 152 in the circuit of FIG. 6, which circuit is included in recorder 24. The amplified outputs from the log amplifiers are compared in a level comparator 154 for amplitude differences. The comparator 154 provides output signals which distinguish the subject's speech from the speech of others, and such signals are applied to bus 58 to be carried to multiplexer MUPX and to be recorded in recorder 24 in digital form. The circuit of FIG. 6 also includes a timer 156 which provides time signals for timing the duration of speech components of the subject and of others. The speech of the subject and the speech of others may be distinguished because of amplitude differences, as shown in the representation of FIG. 7.

Figure 8:
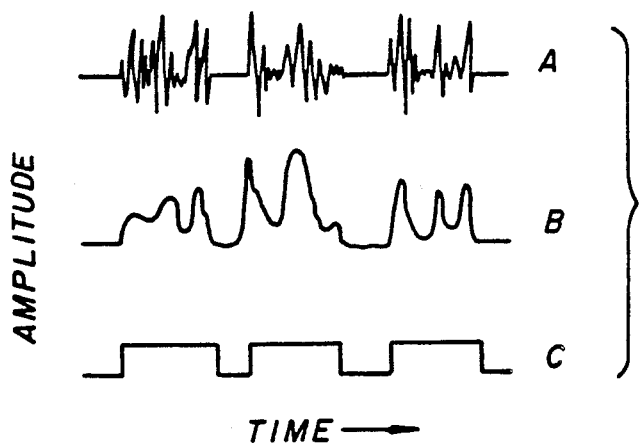
FIG. 8 is a series of curves representing the voice pattern of the subject of FIG. 1 during normal conditions.
Figure 9:
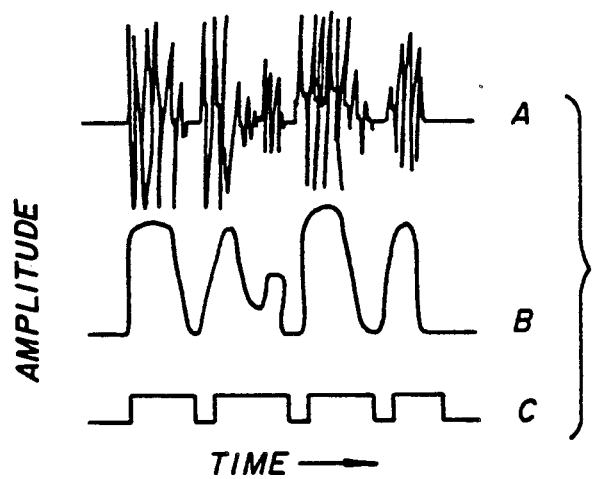
FIG. 9 is a series of curves showing the voice pattern of the subject of FIG. 1 during emotional conditions.

The normal voice of the subject 18, when not under emotional stress, is represented by curves A, B and C in FIG. 8; and the voice of the subject when under emotional stress is represented by the curves of FIG. 9. The speech of the subject and its emotional content is detected by the duty cycle of the sound envelopes, and this is achieved by comparing the ratios of the on and off times of the speech of the subject. That is, as the subject becomes emotional there will be less space between the words and the words will be shorter. it is also desirable to include an amplitude detector, since a raised voice is a usual concomitant of emotion.

Figure 10A:
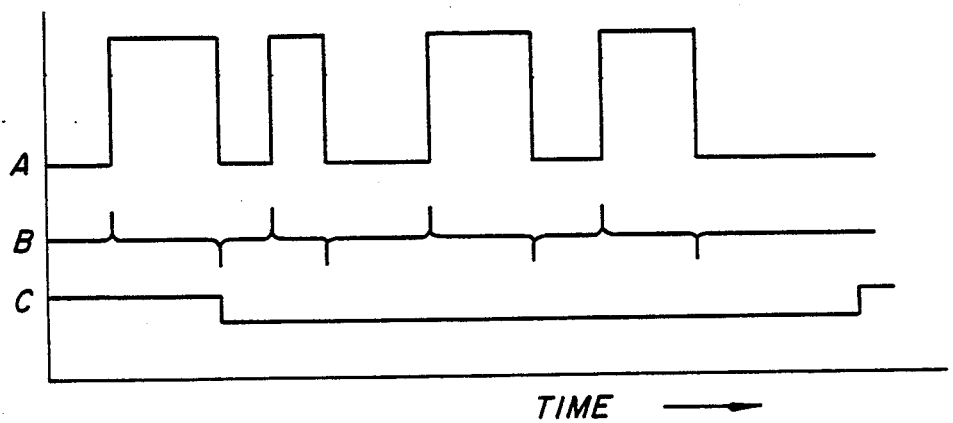
FIG. 10A is a series of curves useful in explaining the operation of the circuit of FIG. 10.
Figure 10:
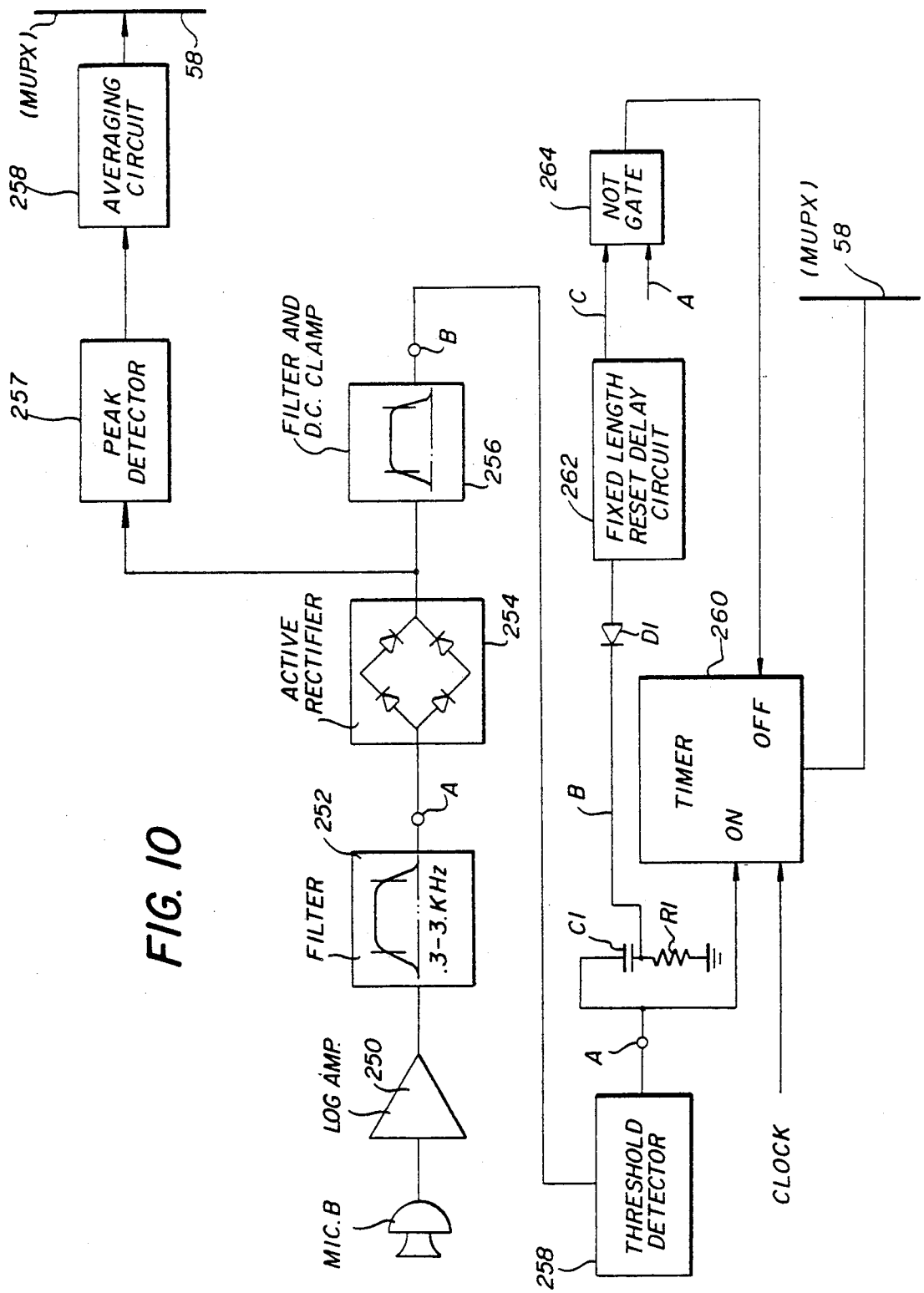
FIG. 10 is a block diagram of a circuit which responds to the voice pattern of the subject to determine the emotional state of the subject.

A circuit for detecting the emotional content of the speech of the subject is included in recorder 24, and a typical circuit is shown in block diagram in FIG. 10. In FIG. 10, the microphone Mic "B" is connected to a log amplifier 250 which, in turn, is connected through a bandpass filter 252 to a precision active rectifier 254. The output of rectifier 254 is passed through a filter and DC clamp circuit 256 to a threshold detector 258. The threshold detector is connected to the "on" input of a timer 260 which measures the on time of the speech.

The "Off" time must be limited after an "On" cycle, otherwise it will count long periods, for example, between sentences. Such limitation is achieved by a fixed length delay circuit 262 and a "Not" gate 264. The output of the "Not" gate is connected to the "Off" input of timer 260. The output of threshold detector 258 is also applied to a differentiating circuit C1, R1, which is connected to delay circuit 262 through a diode D1.

Curves A, B & C of FIG. 10A represent the waveform of the various signals in the circuit of FIG. 10. Curve A is the on/off signal, which is differentiated by the differentiator C1, R1 to generate a negative-going trigger (curve B) each time signal A goes negative. Trigger signal B triggers delay circuit 262 at time intervals longer than the usual delay between words. Delay circuit 262 is reset by each negative trigger B, and when it is not reset, its output C is high.

Timer 260 is turned on whenever signal A is low, and it is turned off whenever signal A low. Should signal A remain low after a predetermined time interval established by delay circuit 262, it is turned off by trigger C going high while signal A is low by virtue of "not" gate 264.

As shown, the normal voice and emotional voice of the subject appears at the output of filter 252, as represented by the curve A in each of the diagrams of FIGS. 8 and 9. The rectified waveforms B of FIGS. 8 and 9 appears at the output of the filter and clamp circuit 256 in FIG. 10, and that output is transformed into a series of pulses by threshold detector 258, the pulses being shown by curves C in FIGS. 8 and 9. The closer the pulses in the curves C are together, and the shorter the pulses, the more emotional is the speech of subject 18. Pulses from the threshold detector 258 are applied to the timers 260 and 262, and a reading of the on time and off time of each of the pulses is fed to the multiplexer over bus 58 to be recorded in recorder 24.

The circuit of FIG. 10 also includes a peak detector 257 and an averaging circuit 258, which serve as an amplitude detector for the reasons stated above.

Figure 11:
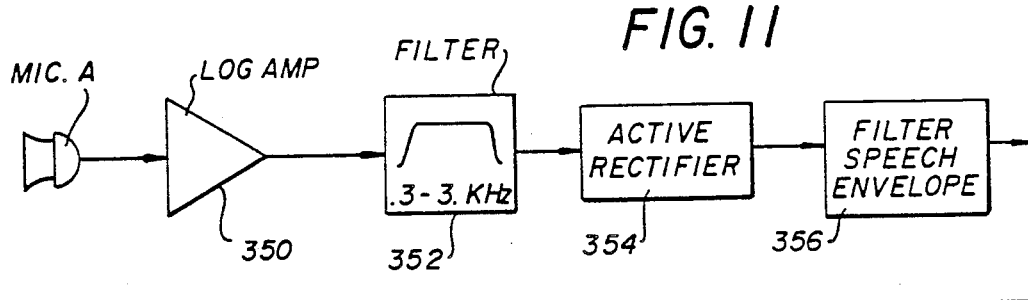
FIG. 11 is a block diagram of a circuit for detecting the incidence of speech from others apart from the subject and also for detecting ambient noise.

As mentioned above, the speech of others and external noise is detected by microphone Mic "A", and is processed by the circuit of FIG. 11. Microphone Mic "A" is connected to a log amplifier 350 which, in turn, is connected through a bandpass filter 352 to an active rectifier 354. The output of the active rectifier is passed through a filter 356 whose out put, in turn, is passed to a detector 358. Output of detector 358 is connected to a timer 360 whose output, in turn, is fed to the multiplexer MUPX over bus 58.

The circuit of FIG. 11, as described in Copending application Ser. No. (K3423), provides an output presentative of the presence of the speech of others, and the emotional content of the speech. Noise is determined by the presence of a continuous background which results in an output from microphone Mic "A" which is of greater amplitude than the output of microphone Mic "B".

As mentioned above, the multiple sensor 22 of FIG. 1 which is mounted on the neck of subject 18 also contains a simple photodiode which is encoded into several light levels so that signals representing ambient light levels may be applied to bus 58 and transmitted to multiplexer MUPX. As also mentioned, temperature readings are provided by including a thermistor in sensor 22 and by applying its output to bus 58. The posture of the subject is also detected by applying signals from the posture sensors SW1 and SW2 of FIG. 1 to bus 58, and utilizing the signals in the manner described in U.S. Pat. No. 4,830,021.

In the foregoing manner, and as described and claimed in Copending application Ser. No. (K3423), all of the augmented data from sensors 20, SW1, SW2 and 22 in FIG. 1 is multiplexed and recorded in digital form on recorder 24. Accordingly, the data collected by the system described above includes physical activity which requires increased heart work. The largest load in the usual subject is walking-jogging-running (locomotor activity). The monitoring of such activity is described in U.S. Pat. No. 4,830,021 which discloses a system by which such activity may be accurately detected and recorded.

In addition to physical activity, the monitoring system of the invention serves to detect and record emotional events. These emotional events are detected and recorded in the system of the invention directly, rather than relying on questionable and variable data such as galvanic skin response, as is sometimes used in the prior art. Two events known to be frequently associated with emotional stress are recorded, as described, and these comprises the presence of subject's speech and conversation, as well as dream states. The voice patterns are analyzed for emotional indicators.

Other conditions known either to effect cardiac activity or which may define cardiac activities are also recorded, and these include subject posture, that is lying, sitting, standing; as well as ambient conditions such as air temperature and ambient light level.

Correlation of the data referred to above yields a substantial amount of information on the subject's activity and environment. As mentioned above, an important feature of the analysis is that it does not attempt absolute determination but rather provides a statistical statement, using estimated or known correlation coefficients from the various inputs. That is, the probability of an event will be provided to the physician. Traditionally, data has been more or less continuously recorded on tape in cardiovascular monitoring systems and processed on replay. However, there are too many sources in the present system to render such an approach feasible. While processing portions of the data before recording and recording others is possible, pre-processing and digital recording represent the most practical approach.

An important feature of the system of the invention in one of its aspects is its ability to correlate, analyze and process data from the various sources. For example, the capability of processing and cross-correlating data from seven sources (EKG, time, locomotor activity, sound, light, temperature and posture) permits one hundred forty-nine combinations, even though not all may be useful. Moreover, since multiple parameters may be extracted from each source, the process is generic rather than comprehensive.

Another important feature of the system of the invention is the reduction of the data to the minimum required by the user. This reduction of data will now be described for each of the parameters recorded.

A. STEP RATE

Step rate is arbitrarily broken into several categories.
5–50 steps/minute . . . random steps
50–120 steps/minute . . . walking
50–80 steps/minute . . . walking slowly
80–120 steps/minute . . . walking quickly
120–200 steps/minute . . . running
120–150 steps/minute . . . running slowly
150–200 steps/minute . . . running quickly.

Figure 12:
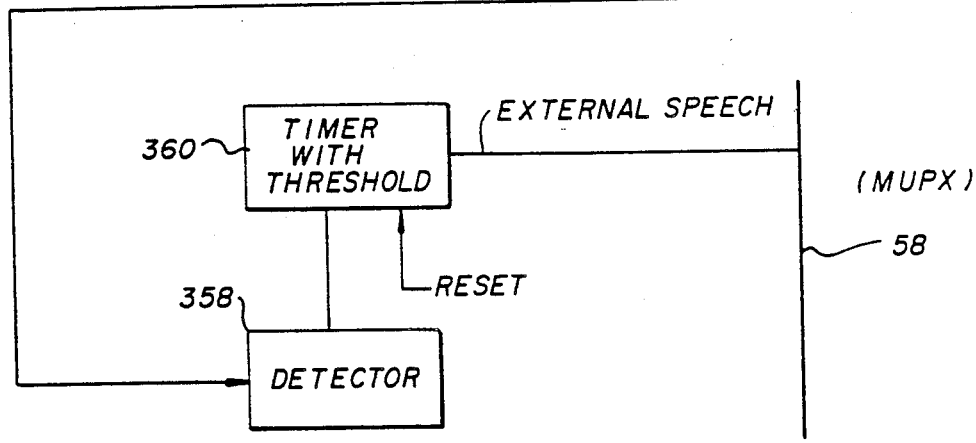
FIG. 12 is a series of curves illustrating the probable ambulatory state of the subject derived from a reading of his or her step rate.
Figure 12:
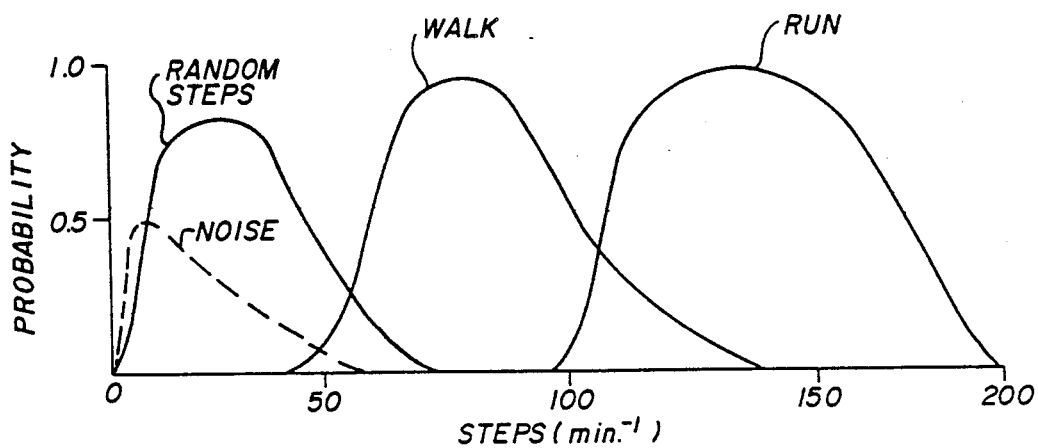

Taken alone, the above parameters have varying probabilities which are shown in the curves of FIG. 12. This data forms part of the analysis program.

Figure 13:
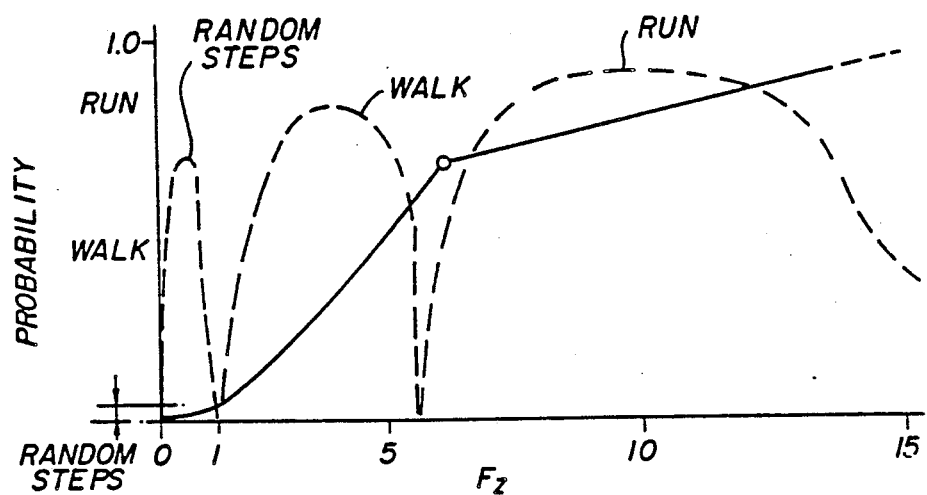
FIG. 13 is a series of curves for further illustrating the ambulatory state of the subject further enhanced by a measure of the vertical forces generated by the subject.

To increase the reliability of the system, vertical force (Fz) should also be used. The monitoring of such force is described in detail in U.S. Pat. No. 4,830,021. The characteristic of the vertical force (Fz) is shown with a probability curve in FIG. 13.

By combining the probabilities from the step rate and Fz parameters much higher reliability can be obtained especially in the transition zones between the step-walk-run states. For example, if step rate were used alone, there would be no detection of jumping by the subject so that an anomaly could arise. However, jumping would be detected by the resulting large Fz occurring at low step rates.

B. POSTURE

The posture signal can provide information in its own right as well as adding reliability to other signals. For example, only in the standing position can one engage in normal locomotor activity. Sleep is more likely when lying but would almost never occur standing.

C. TIME

Time is an imperative signal for identifying and coordinating activities, but it can also be a valuable adjunct signal in analysis. For example, the probability of sleep is much higher in hours just prior and following midnight, while locomotor activity is much lower.

It should be noted that if the subject reliability reports events and times, this additional data could be manually entered into the computer. For example, if the patient reliablty states he went to bed at 2230 hours and got up at 0645 hours, this information can be manually entered and used in correlation.

D. LIGHT

Signals representing light are indicative of the environment, especially when used with other data. For example, above a certain light level and time of day, there is a high probability that the subject is n sunlight, whereas an indication of total darkness suggests the likelihood that the subject is asleep.

E. TEMPERATURE

This is a useful signal in its own right for its affects heart rate but it may be an indicator of indoors versus outdoors.

F. VOICE/SOUND

The discrimination between external speech, subject speech and subject speech with emotion has been described above. Conversation has certain probabilities when the subject and external speech are present.

All of the foregoing functions are processed by the computer which first stores the data, as described above, and then indexes the data for correlation to EKG events. The computer could also perform individual characterizations and normalizations of data, for example, to establish averages or totals for data such as 10,400 steps/day at 130 steps/minute; or to establish normal subject voice levels and speech duty cycles such that individual deviations become more significant.

It is also important for the computer to correlate normal and abnormal events with conditions, even or in some cases especially to EKG events. For example:

| EKG | Parameter/(Probability) | |
|---|---|---|
| Tachycardia | Running | +.92 |
| | Walking | +.85 |
| | Sleep REM | +.80 |
| | Speech, subj (emotion) | +.72 |
| | Temperature | +.3 |
| | Sleep | −.8 |
| Ventricular | Sleep REM | .9 |
| Tachycardia | Speech, Subj. Emotion | .8 |
| | Tachycardia | .8 |

The computer may provide a printed record of the augmented Holter monitoring such as the following:

| Time | Event | Condition |
|---|---|---|
| 1600–1643 | Tachycardia 120–160 BPM | Running 140–160 Steps/min (95) Outdoors (0.89) Temperarure 30° C. |
| 1930–35 | Ventric Tachycardia 180 BPM | Conversation 0.83 Speech Subj. (.95) Emotion (.80) Seated (.95) Indoors (.60) |
| 0320–25 | Ventric Tachycardia 180 BPM | Sleep (.93) REM stage (.88) Lying (.95) |
| | Etc. | |

Figure 14:
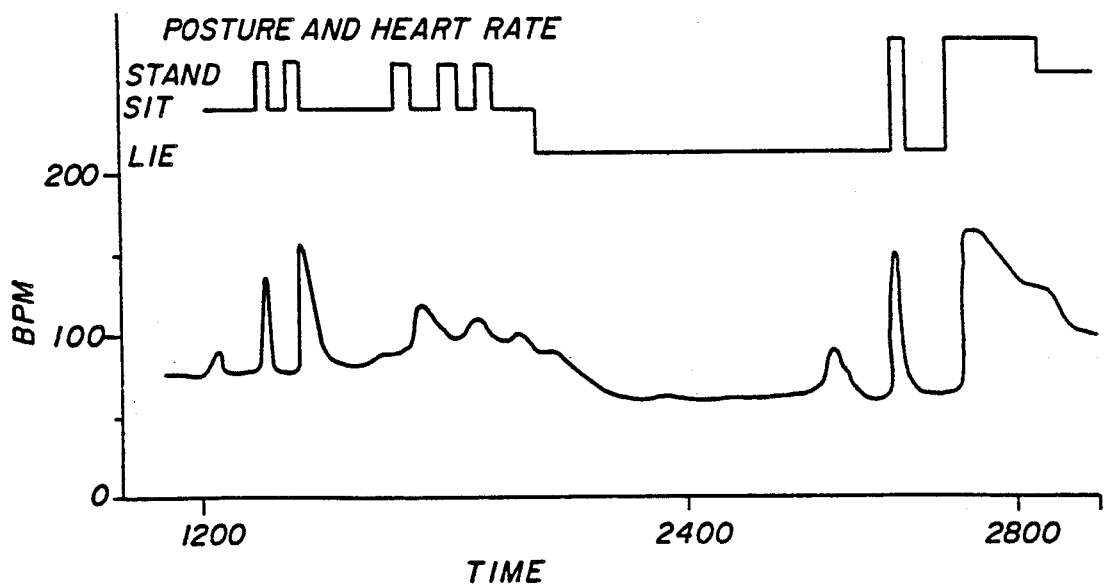
FIG. 14 is a series of curves illustrating results obtained by the system of the invention in graphic form.

When desired a complete graphic or other record may be made available by the computer, as shown in FIG. 14.

The invention provides, therefore, an improved monitoring system for detecting and processing parameters affecting the cardiovascular system. The monitoring system of the invention, as described above, includes a conventional Holter EKG recorder for long term electrocardiograph monitoring of a subject. In addition, and in accordance with the concepts of the invention, the monitoring system includes sensors responding to physical and emotional activities of the subject for generating electric signals representative of such activities. These latter electric signals are recorded in a separate recorder, or along with the EKG signals in the Holter recorder. The monitoring system of the invention includes a signal processor for reducing the data represented by the electric signals and for correlating the data with the electrocardiogram data represented by the EKG signals from the Holter recorder.

One example of cross correlation is described above, however many more are possible. It must be emphasized that the probability of a correct diagnosis is increased by repeated correlations or external conditions with respect to some abnormality, for example, repeated S.T. depression. Moreover, heart rate change may be correlated with respect to posture change and compared with standards. In addition, events of the heart (EKG) may be cross-correlated. For example, S.T. depression with respect to heart rate and fixed occlusions would more likely be associated with tachycardia, whereas spasm could occur at any rate.

It will be appreciated that while a particular embodiment of the invention has been shown and described, modifications may be made. It is intended in the claims to cover all such modifications which come within the true spirit and scope of the invention.

I claim:

1. A monitoring system for detecting and processing parameters affecting the cardiovascular system of a subject and for correlating the parameters with the EKG of the subject, said monitoring system including: EKG sensor means for generating EKG signals relating to a subject; second sensor means for detecting selected activities of the subject and for generating electric signals corresponding thereto; and processing means responsive to said EKG signals and to said electric signals from said second sensor means for correlating said electric signals from said second sensor means with predetermined values to yield statistical information related to the activities of the subject and to correlate said information with the EKG signals generated by said EKG sensor means.

2. The monitoring system defined in claim 1, in which said second sensor means detects selected physical and emotional activities of the subject.

3. The monitoring system defined in claim 2, in which said second sensor means detects the posture of the subject.

4. The monitoring system defined in claim 2, in which said second sensor means detects selected ambient conditions.

5. The monitoring system defined in claim 1, and which includes electromagnetic recorder means connected to said EKG sensor means and connected to said second sensor means for recording the EKG signals and the signals generated by said second sensor means.

* * * * *